United States Patent
Stewart et al.

(10) Patent No.: US 7,387,994 B2
(45) Date of Patent: Jun. 17, 2008

(54) COMPOSITIONS AND METHODS FOR PRODUCING VASCULAR OCCLUSION USING A SOLID-PHASE PLATELET BINDING AGENT

(75) Inventors: Michael W. Stewart, St. Albert (CA); Antoine Noujaim, Edmonton (CA); Roland H. Person, Edmonton (CA)

(73) Assignee: ViRexx Medcial Corp., Edmonton, Alberta (CA)

( * ) Notice: Subject to any disclaimer, the term of this patent is extended or adjusted under 35 U.S.C. 154(b) by 4 days.

(21) Appl. No.: 11/205,047

(22) Filed: Aug. 17, 2005

(65) Prior Publication Data

US 2005/0287189 A1    Dec. 29, 2005

Related U.S. Application Data

(63) Continuation of application No. 10/241,717, filed on Sep. 12, 2002, now Pat. No. 6,960,352.

(60) Provisional application No. 60/318,339, filed on Sep. 12, 2001.

(51) Int. Cl.
*A61K 38/00* (2006.01)
*A61K 9/14* (2006.01)
*A61F 2/00* (2006.01)

(52) U.S. Cl. .............. 514/2; 514/12; 424/422; 424/489; 424/490; 424/499; 424/501

(58) Field of Classification Search ............ 514/2, 514/12; 424/422, 489, 490, 499, 501
See application file for complete search history.

(56) References Cited

U.S. PATENT DOCUMENTS 6,960,352 B2 * 11/2005 Noujaim et al. ............ 424/423

OTHER PUBLICATIONS

Sundfor,K. et al. Gynecologic Oncology [1997] 64:230-236.*

* cited by examiner

*Primary Examiner*—Christina Chan
*Assistant Examiner*—F. Pierre VanderVegt
(74) *Attorney, Agent, or Firm*—William J. Bundren

(57) ABSTRACT

The present invention relates generally to methods and compositions for targeting and delivering solid-phase platelet-dependent vascular occlusion agents. In particular, particles or coils or stents coated with platelet binding agents are directed to target vasculature, such as the vasculature of solid tumor masses or AV-malformations or aneurysms or endoleaks; the solid-phase agent then binds and activates platelets, which in turn bind and activate other platelets. This process results in the rapid formation of a platelet-mediated thrombus about the solid-phase agent causing vessel occlusion.

51 Claims, No Drawings

COMPOSITIONS AND METHODS FOR PRODUCING VASCULAR OCCLUSION USING A SOLID-PHASE PLATELET BINDING AGENT

This application is a continuation of U.S. application Ser. No. 10/241,717 filed Sep. 12, 2002 now U.S. Pat. No. 6,960,352, which is a non-provisional of U.S. Application Ser. No. 60/318,339 filed Sep. 12, 2001. These patent applications are hereby incorporated by reference.

I. BACKGROUND OF THE INVENTION

The present invention is directed to compositions and methods for producing a therapeutic benefit by producing vascular occlusion using platelet activation as the initiating event. Compositions and methods of the invention involve delivering a solid-phase platelet-binding agent to a target site, causing platelets to bind and activate thereby forming a localized thrombus. Occlusion of the vasculature of the target tissue by the localized thrombus results in deprivation of essential oxygen and nutrients, in turn leading to tissue regression and ultimately tissue death.

II. DESCRIPTION OF RELATED ART

Platelets function in the body to limit blood loss in the event of vascular damage. Normally, platelets circulate throughout the body with other cellular components of blood, bathed in a mixture of various plasma proteins, many of which play key roles in the clotting process. Upon exposure of vascular sub-endothelium, a complex series of events occurs to limit the loss of blood from the damaged vessel. Circulating platelets contacting components of the exposed sub-endothelium: 1) bind and adhere, 2) spread across the exposed surface, 3) activate as evidenced by release of granule contents, 4) aggregate and recruit other circulating platelets from the blood stream, and 5) form an efficient plug, clot, and/or thrombus stemming the flow of blood from the vessel.

In response to vascular injury, such as atherosclerotic plaque rupture in a coronary vessel, circulating platelets are exposed to a variety of matrix elements that are prothrombotic. Platelets can strongly adhere to two specific matrix components, collagen and von Willebrand factor. At low blood flow shear rates, adhesion to collagen predominates, whereas at higher shear rates—for example, those that would occur in stenosed vessels—the initial platelet adhesion is primarily mediated by binding to von Willebrand factor. Adhesion to either collagen and/or von Willebrand factor initiates signals leading to platelet activation, platelet spreading on the matrix, secretion of prothrombotic substances such as adenosine diphosphate (ADP) and thromboxane $A_2$, and upregulation of the adhesive function of GP IIb-IIIa, which can bind fibrinogen and von Willebrand factor, resulting in platelet aggregate or thrombus formation.

In contrast to the coagulation cascade, a process defined in part by the conversion of fibrinogen to fibrin, platelets coalesce about the damaged area and are held together by bridging molecules that bind to specific receptors on the platelet surface. The initial bridging between platelets and the subendothelium is dependent on the interaction between the glycoprotein Ib (GPIb) receptor on the surface of the platelet and von Willebrand Factor (VWF) in the subendothelium (i.e., immobilized VWF). This interaction in itself is unique, since normal platelets circulating in the blood often contact soluble VWF, but are not activated, nor do they bind to the soluble VWF. In vitro experimentation has confirmed that immobilization of the soluble VWF to a surface facilitates binding and activation of platelets. Upon activation of the platelet, an additional receptor, glycoprotein IIb/IIIa (GPIIb/IIIa), is altered enabling the binding of several plasma proteins, thereby promoting platelet/platelet binding.

Hyperactive platelets can induce thrombus formation at inopportune times resulting in reduced blood supply to various organs and tissues. A prime example is thrombus formation induced by blood flowing through a stenotic (narrowed) vessel supplying the heart. Reduction of the flow of blood to the heart muscle leads to infarction and eventually heart attack (cardiac cell death). Cerebral ischemia (transient ischemic attack (TIA); stroke) occurs when an embolus or thrombus occludes blood vessels feeding the brain.

Other pathological states exist that are caused by platelet activation as a result of an inappropriate antibody-mediated process. Heparin-induced thrombocytopenia (HIT) is characterized by a dramatic loss in platelet numbers and thrombus formation at sites of pre-existing pathology. From 1% to 5% of all patients receiving unfractionated heparin as an anticoagulant to promote blood flow produce an antibody that binds to heparin in complex with a platelet granule protein. The binding of the antibody to the heparin/protein complex on the surface of the platelet induces rapid platelet activation and localized thrombus formation. This in turn leads to infarction of the affected area.

Thrombosis is a well-described consequence of cancer. Controversy exists as to whether the presence of a hypercoagulable state is predictive of cancer. Many studies have been conducted demonstrating a prothrombotic tendency with most neoplasia or neoplasms. It has been suggested that thrombosis is the most frequent complication with patients with overt malignant disease.

A key to the development of successful anti-tumor agents is the ability to design agents that will selectively kill tumor cells, while exerting relatively little, if any, untoward effects against normal tissues. This goal has been elusive in that there are few qualitative differences between neoplastic and normal tissues. Because of this, much research over the years has focused on identifying tumor-specific "marker antigens" that can serve as immunological targets both for chemotherapy and diagnosis. Many tumor-specific or quasi-tumor-specific (tumor-associated) markers have been identified as tumor cell antigens that can be recognized by specific antibodies.

Unfortunately, it is generally the case that tumor-specific antibodies will not in and of themselves exert sufficient anti-tumor effects to make them useful in cancer therapy. In contrast with their efficacy in lymphomas, immunotoxins have proven to be relatively ineffective in the treatment of solid tumors such as carcinomas. The principal reason for this is that solid tumors are generally impermeable to antibody-sized molecules: specific uptake values of less than 0.001% of the injected dose per gram of tumor are not uncommon in human studies. Furthermore, antibodies that enter the tumor mass do not distribute evenly for several reasons. Firstly, the dense packing of tumor cells and fibrous tumor stromas present a formidable physical barrier to macro-molecular transport and combined with the absence of lymphatic drainage create an elevated interstitial pressure in the tumor core which reduces extravasation and fluid convection. Secondly, the distribution of blood vessels in most tumors is disorganized and heterogeneous. As a result some tumor cells are separated by large distances from capillaries so that the extravasating antibody must diffuse over a large volume in order to reach and bind to remote tumor cells. Thirdly, all of the antibody entering the tumor may become absorbed in perivascular regions by the first tumor cells encountered, leaving none to reach tumor cells at more distant sites.

One approach to overcoming the deficiencies of targeting tumors with antibodies would be to target thrombus-inducing agents to the vasculature of the tumor rather than to the tumor.

The present inventors propose that this approach will provide several advantages over targeting tumor cells directly. Firstly, the target cells are directly accessible to vascularly administered therapeutic agents permitting rapid localization of a high percentage of the injected dose. Secondly, since each capillary provides oxygen and nutrients for thousands of cells in its surrounding cord of tumor, even limited damage to the tumor vasculature could produce an avalanche of tumor cell death.

The present invention is also directed to compositions and methods of treating abnormal tissue growth, abnormal bleeding (during or after surgery, postpartum), ectopic pregnancy, placenta previa, placenta accreta and uterine fibroids.

Under certain clinical situations, inhibition of blood flow to a tissue through occlusion of its associated vasculature is desirable. Examples include hemorrhagic stroke, existence of saphenous vein side branches in saphenous bypass graft surgery, treatment of aortic aneurysm, correction of vascular malformations, and treatment of solid tumors.

Vascular occlusion has been performed using a variety of techniques and materials including embolotherapy. Examples of embolotherapy include the use of particles composed of a variety of materials including polyvinyl alcohol (Boschetti, PCT WO0023054), acrylamide (Boschetti et al, U.S. Pat. No. 5,635,215; Boschetti et al, U.S. Pat. No. 5,648,100), polymethyl methacrylate (Lemperle, U.S. Pat. No. 5,344,452), physical plugs composed of collagen (Conston et al, U.S. Pat. No. 5,456,693) and coils (Mariant, U.S. Pat. No. 5,639,277). Embolotherapy involves the delivery of these materials to the target vasculature by means of a catheter. Since the vasculature in any given area proceeds from larger arteries to arterioles to metarterioles to capillaries, each with progressively smaller vessel diameters, the delivered material (embolus) continues to travel in the flowing blood until it becomes lodged in the smaller blood vessels thereby impeding the flow of blood to the dependent tissue.

The present invention is novel and addresses unmet medical needs through the use of a solid-phase material, such as microparticles or coils or stents, coated with porous polylactide, polyglycolide or polylactide-co-glycolide particles coated with mammalian collagen. In this way a therapeutic benefit may be achieved by delivering a solid-phase platelet-binding agent to a target site and initiating efficient thrombus formation leading to occlusion of the associated vasculature.

III. SUMMARY OF THE INVENTION

The present invention relates to therapeutic methods and compositions for targeting tissues and/or organs, and associated vasculature, which are hyperplastic or neoplastic in nature, or which have arterio-venous malformations, or which are hemorrhaging, using solid-phase agents that induce thrombus formation via localized platelet activation. The composition comprises an agent for capturing platelets on a solid-phase agent such as a coil or a stent or a particle. In some embodiments of the invention, the solid-phase agent both captures and activates the platelets. The method utilizes localizing platelet collection and activating the platelets on the solid-phase particle to produce subsequent thrombus formation, thereby limiting the blood supply to the target area, without inducing a generalized or systemic pro-thrombotic state.

Purposeful induction of thrombosis in a patient appears at first glance to be counter-intuitive, since thrombosis is well known to contribute significantly to patient morbidity and mortality. The present invention, solid-phase platelet-mediated occlusion, is based on the site-specific induction of thrombosis utilizing the body's natural capacity to produce a thrombus in response to porous polylactide, polyglycolide or polylactide-co-glycolide particles coated with mammalian collagen or other locally acting platelet activation agents. The immobilized collagen, acting as a platelet binding agent, serves to anchor platelets to the particles through two mechanisms: 1) directly, by binding to key platelet membrane receptors such as $\alpha2\beta1$ and GPVI; and 2) indirectly, by capturing circulating, autologous, von Willebrand factor (VWF), which in turns captures and activates platelets circulating in the blood stream through key platelet membrane receptors such GPIb and GPIIb/IIIa. Although VWF circulates in the blood stream in soluble form, it is not until the molecule is exposed as part of the subendothelium or binds to exposed collagen from the subendothelium that it is capable of capturing platelets and inducing platelet activation.

Contact of the solid-phase platelet-binding agent with the blood from a patient (ex vivo) or in the blood stream (in vivo) induces platelet binding and localized activation leading to accretion of platelets about the solid-phase agent leading to thrombosis and cessation of blood flow to the tissue supplied by the occluded blood vessel(s). Cells, including tumor cells or hyperplastic tissue, diminish or die as a result of loss of localized blood flow. This approach avoids systemic platelet activation and thrombosis; relying on the fact that porous polylactide, polyglycolide or polylactide-co-glycolide particles coated with mammalian collagen binds to and activates circulating platelets. Thus, the methods and compositions of the present invention are an indirect means of treating a pathological condition, such as cancer, hyperplastic cells, excessive bleeding or arteriovenous (AV) malformations.

The present invention improves on existing methods for treating solid tumors, hyperplastic tissue, excessive bleeding and AV-malformations and any other disease or condition in which platelets (resting and/or activated) may play a therapeutic role.

In a manner similar to an existing pathological condition (i.e. Heparin-Induced Thrombocytopenia [HIT]), localized platelet activation can be enhanced by means of an Fc-mediated process by including or incorporating a human Fc fragment onto the solid-phase agent, or by directing select antibodies to the target area. Platelet activation in HIT syndrome results in localized thrombosis and cessation of blood flow to the affected area. This leads to death of the affected tissue.

The extent or degree of site-specific thrombosis can be controlled in a variety of ways. Inhibition of platelet activation through the use of anti-platelet agents (e.g. GPIIb/IIIa inhibitors, aspirin, dipyridamole, etc.) decreases the propensity to induce a thrombus in a defined, titratable manner. Altering local blood flow, blood pressure and tissue temperature can also serve as means of controlling local platelet activation to a stimulus.

Typical vascularized tumors are the solid tumors, particularly carcinomas, which require a rich vascular blood supply. Exemplary solid tumors to which the present invention is directed include, but are not limited to, primary malignant tumors of the lung, breast, ovary, stomach, pancreas, larynx, esophagus, testes, liver, parotid, biliary tract, colon, rectum, cervix, uterus, endometrium, kidney, bladder, prostate, thyroid, head and neck, melanomas, gliomas, neuroblastomas, neuroendocrine tumors, and the like. Other conditions to which the present invention is directed include, but are not limited to, secondary (metastatic) tumors of the above mentioned tumor types, cancer pain, AV-malformations, uterine fibroids, pelvic congestion, menorrhagia, varicoceles, hemoptysis, aneurysms, visceral artery aneurysms, pseudoaneurysms and endoleaks.

A preferred method of the invention includes preparing a coil or stent coated with porous polylactide, polyglycolide or polylactide-co-glycolide particles coated with mammalian collagen (PLGA/Collagen) and introducing the PLGA/Collagen-coated agent into the bloodstream of an animal, such as a human patient, an animal patient, or a test animal; the PLGA/Collagen is then delivered or collects at a desired target site. The coils or stents can be constructed of any suitable material capable of retaining PLGA/Collagen either within the coil or stent or on the surface of the coil or stent for an indefinite or varying lengths of time.

A solution to the problem of the unrestrained growth of solid tumors is to attack the blood vessels in the tumor. This approach offers several advantages over methods that directly target tumor cells. Firstly, the tumor vessels are directly accessible to vascularly administered therapeutic agents, thus permitting rapid localization of high percentage of the injected dose. Secondly, since each capillary provides oxygen and nutrients for thousands of cells in its surrounding cord of tumor even limited damage to the tumor vasculature could produce extensive tumor cell death. Finally, blood vessels are similar in different tumors, making it feasible to develop a single reagent for treating numerous types of cancer.

IV. DESCRIPTION OF THE DRAWINGS

Not Applicable

V. DETAILED DESCRIPTION OF THE INVENTION

The present invention provides compositions and methods for capturing platelets at a predetermined site, activating the platelets, and harnessing the natural function of platelets to achieve a beneficial therapeutic result. In accordance with the present invention, the platelets may be circulating platelets or may be platelets obtained from an external source. In accordance with the present invention, platelets may be targeted to a specific site, and then the natural ability of platelets to induce thrombus formation may be used to interrupt, disrupt, or reduce blood flow at the site. Reduced blood flow concomitantly reduces nutrient supply to a disease or condition agent, such as a tumor, so the size of the disease agent is diminished. It is clear that reducing the size of a tumor is an obvious therapeutic benefit. In some instances reduction of the blood supply to a target area alleviates pain.

The present invention also includes targeting platelets to a pre-determined tissue capable of being selectively targeted, e.g., hyperplastic tissue, using a solid-phase agent capable of binding and activating the platelets. In these embodiments of the invention, targeting refers to the solid phase containing a targeting moiety, e.g., a ligand or the like, that specifically binds the pre-determined site or tissue. In other embodiments of the invention, targeting may include delivering a composition of the present invention at or near a tumor site, e.g., by catheter, stent, or coil. Activating the platelets at the preselected site causes a therapeutic benefit by reducing the nutrient supply to the tissue or site.

The present invention provides compositions and methods for inducing thrombus formation by capturing platelets on the solid-phase agent, inducing activation of the platelets, and allowing a thrombus to form. Thrombus formation in the target vasculature reduces the blood supply to the downstream tissue. By capturing platelets on a PLGA/Collagen-containing solid phase agent, the compositions and methods of the present invention may be used to treat cancer, hyperplasia, uterine fibroids, pelvic congestion, menorrhagia, AV-malformations, neuro-embolism, varicoceles, hemoptysis, visceral artery aneurysms, arterial aneurysms, endoleaks, and the like. Furthermore, the compositions and methods of the present invention provide a therapeutic benefit to the recipient of the composition.

In a preferred embodiment of the invention, the PLGA/Collagen is of mammalian origin. In a most preferred embodiment of the invention, the PLGA/Collagen is of human origin. In a further most preferred embodiment of the invention, the PLGA/Collagen is of bovine origin.

The PLGA/Collagen may be natural, synthetic, recombinant, or a peptide sequence conforming to a biologically active portion of PLGA/Collagen. In a further most preferred embodiment of the invention, the PLGA/Collagen is of recombinant origin.

The present invention also provides compositions that bind a platelet-binding agent directly or indirectly through a spacer to the solid phase, so long as the ability of the platelet-binding agent to bind platelets is not impaired. Spacer, as used herein, refers to a group of inert or active molecules that physically separate the platelet binding agent from the surface of the solid phase agent. Exemplary spacers are described below. The direct binding can occur either covalently or non-covalently. Indirect binding can occur through spacers, including but not limited to peptide spacer arms, antibody spacers, antibody fragment spacers, fusion protein spacers or carbohydrate spacers. These spacers normally act only as bridges between the particle and the PLGA/Collagen; however, the spacers could also be used to alter the degree of platelet activation. For example, an Fc component could be used as a spacer, thereby effecting enhanced platelet activation on and about the solid-phase agent. Coupling of PLGA/Collagen to the solid phase agent can occur using methods known to those skilled in the art. Examples of coupling agents include but are not limited to glutaraldehyde and carbodiimide.

In a preferred embodiment of the invention, the positioning within the vascular system of mammals of compositions without an active targeting agent would be selected by blood flow directed positioning following delivery by means of a superselective microcatheter.

Compositions according to the present invention may also include a targeting agent or moiety capable of binding a target antigen or site on the vascular endothelium or target tissue, thereby enabling localization of the solid-phase agent to a selected site. Exemplary targeting agents or moieties are well known to those skilled in the art, and include, but are not limited to antibodies, ligands, receptors, hormones, lectins, and cadherins, or portions or fragments thereof.

In a preferred embodiment of the invention, the targeting agent would include an antibody or antibody-like molecule with biotin, biotin mimetic and/or a peptide component. In a further preferred embodiment of the invention, the antibody or antibody-like molecules would be directed toward a growth factor/receptor complex.

Compositions according to the invention may also include one or more of the following: one or more platelet binding modulators (e.g., inhibitors or enhancers), one or more thrombus formation controllers or modulators or one or more complement cascade components.

Methods according to the invention may also include administering a solid-phase agent capable of binding platelets at a pre-determined site; may also include inducing activation of the captured platelets; administering a bifunctional binding agent having an antigenic determinant and a platelet binding site; controlling thrombus generation by altering the temperature of one or more compositions of the invention, or by altering the temperature at the pre-selected site.

Methods according to the invention may further include one or more of the following: administering one or more platelet binding modulators, administering one or more thrombus formation modulators; administering one or more complement cascade components; administering one or more ligands and/or anti-ligands for binding the solid phase to a pre-determined site, and/or for binding a platelet binding moiety or component to the solid phase.

The present invention also includes a kit which may contain but is not limited to any or all of the following components including a solid-phase agent for targeting platelets to an endothelial membrane component: a binding agent for binding platelets; a ligand for binding an endothelial membrane component; a ligand conjugate; an anti-ligand for binding the ligand or the ligand conjugate; a platelet binding modulator (enhancer and/or inhibitor); a thrombus formation modulator; a complement cascade component; a complement cascade component inducer; and a binding agent for binding platelets that includes an anti-ligand. The kit may include a bifunctional binding agent, and/or a binding agent-ligand conjugate, and/or a platelet-binding agent-anti-ligand conjugate.

The compositions and methods of the present invention include any mechanism of delivering a composition to the pre-selected site, including but not limited to systemically, locally, orally, or topically.

In accordance with some embodiments of the invention, binding agents are used to capture platelets at a predetermined site.

Definitions:

As used herein, a solid-phase agent refers to any solid material suitable for binding, containing, or retaining a platelet-binding agent. The platelet-binding agent may be attached to the solid-phase agent such that platelet binding activity is retained, e.g., at or within a target site. The solid phase agent may be a coil, stent, or particle, e.g., a bead or the like, all of which are well known to those skilled in the art.

As used herein, a particle refers to a discrete portion or part of a solid-phase material capable of containing or retaining a platelet-binding agent.

A preferred method of the invention includes preparing a particle coated with PLGA/Collagen of recombinant or mammalian origin and introducing the PLGA/Collagen-coated particle into the bloodstream of an animal, such as a human patient, an animal patient, or a test animal.

As used herein, the term "particle" refers to any solid-phase material capable of binding platelets, either directly or indirectly (e.g., through ligands). The particles can be homogenous or heterogeneous as related to size. Specifically, the particles can be of spherical (including ovoid) or irregular shape. The particles can be constructed of any suitable material capable of retaining collagen either within the particle or on the surface of the particle for an indefinite or varying lengths of time. Exemplary materials include polyvinyl alcohol (PVA), polystyrene, polycarbonate, polylactide, polyglycolide, lactide-glycolide copolymers, polycaprolactone, lactide-caprolactone copolymers, polyhydroxybutyrate, polyalkylcyanoacrylates, polyanhydrides, polyorthoesters, albumin, gelatin, polysaccharides, dextrans, starches, methyl methacrylate, methacrylic acid, hydroxylalkyl acrylates, hydroxylalkyl methacrylates, methylene glycol dimethacrylate, acrylamide, bisacrylamide, cellulose-based polymers, ethylene glycol polymers and copolymers, oxyethylene and oxypropylene polymers, polyvinyl acetate, polyvinylpyrrolidone and polyvinylpyridine, magnetic particles, fluorescent particles, animal cells, plant cells, macro-aggregated and micro-aggregated albumin, denatured protein aggregates and liposomes, used singly or in combination.

In the present invention the preferred solid phase material is polylactide, polyglycolide or polylactide-co-glycolide. The solid phase materials suitable for use in the present invention are well known to those skilled in the art, and should not be limited to those exemplary materials recited above.

Exemplary materials for forming the stent or coil include, but are not limited to: polyvinyl alcohol (PVA), polystyrene, polycarbonate, polylactide, polyglycolide, lactide-glycolide copolymers, polycaprolactone, lactide-caprolactone copolymers, polyhydroxybutyrate, polyalkylcyanoacrylates, polyanhydrides, polyorthoesters, polysaccharides, dextrans, starches, methyl methacrylate, methacrylic acid, hydroxylalkyl acrylates, hydroxylalkyl methacrylates, methylene glycol dimethacrylate, acrylamide, bisacrylamide, cellulose-based polymers, ethylene glycol polymers and copolymers, oxyethylene and oxypropylene polymers, polyvinyl acetate, polyvinylpyrrolidone and polyvinylpyridine; magnetic materials, fluorescent materials; gold, platinum, palladium, rhenium, rhodium, ruthenium, stainless steel, tungsten, titanium, nickel and alloys thereof; used singly or in combination.

The preferred size of the solid phase material depends on the type of material being used. For example, those skilled in the art will recognize that if the solid phase is a stent or coil, the size is preferably of a diameter that fits within a blood vessel, such as an artery. Typically the diameter will be up to about 15 mm or greater. If the solid phase is a particle, such as a bead, the diameter may be up to about 7 mm, preferably from about 1 μm to about 5 mm, even more preferably from about 20 μm to about 300 μm. The size of solid phase materials suitable for use in the present invention are well known to those skilled in the art, and should not be limited to the exemplary sizes recited above.

As used herein, a binding agent or targeting moiety refers to one or more solid phase chemical or biological molecules or structures for binding one substance to another. Specifically the binding agent, or solid phase agent, binds a ligand, a receptor or a ligand/receptor complex on a defined population of cells, typically hyperplastic tissue and/or associated vasculature, or a cancer cell and/or associated vasculature. A molecule's function as a binding agent should not be limited by the structural mechanism of attachment. For example, a binding agent may bind a receptor, an antigenic determinant or epitope, an enzymatic substrate, or other biological structure linking the binding agent to a target cell or cell population. The binding agent may be a conjugate, and includes but is not limited to immunological conjugates, chemical conjugates (covalent or non-covalent), fusion proteins, and the like.

As used herein, a ligand-binding agent refers to a complementary set of molecules that demonstrate specific binding for each other. A ligand/anti-ligand pair generally binds with relatively high affinity, and for this reason, may be highly desirable for use with the present invention. A very well known ligand/anti-ligand pair is biotin and avidin. As used herein, avidin refers to avidin, streptavidin, neutravidin, derivatives and analogs thereof, and functional equivalents thereof. Avidin may bind biotin in a multivalent or univalent manner. Other exemplary ligand/anti-ligand pairs include, but are not limited to, homophyllic peptides, heterophyllic peptides, "leucine zippers", zinc finger proteins/ds DNA fragment, enzyme/enzyme inhibitor, hapten/antibody, ligand/ligand receptor, and growth factor/growth factor receptor.

As used herein, a selected site, a pre-determined site, targeting, and pre-targeting all refer to a site where the accumulation of platelets about a solid-phase agent will provide a therapeutically beneficial result. Typically, this involves target site localization of a targeting moiety. Such sites include, but are not limited to, the vasculature of solid tumors, the vasculature of benign tumors, the vasculature of hyperplastic tissue(s), AV-malformations, vessel aneurysms and endoleaks.

As used herein, delivery of the solid agent comprising a platelet-binding agent can occur using a catheter, a microcatheter or by needle and syringe. Delivery by catheter or microcatheter is most often achieved by access through the arterial circuit, however delivery of the solid agent through the venous circuit is also desirable. As an example, the solid agent in the form of particles, coils or stents can be delivered by catheter to the target site using the arterial or venous circuits. Delivery of the solid agent using the arterial circuit is advantageous since the capillary beds downstream of the applied agent in the target tissue act as a means of trapping the agent, thereby preventing the agent from entering the systemic circulation. The solid agent can also be localized within the arterial circulation using a targeting agent associated with the solid agent. Delivery of the solid agent using the venous system is also desirable. Localized delivery of the solid agent in the venous system can be accomplished by binding the solid agent to the target site using a targeting agent associated with the solid agent. The solid agent can also be delivered to the target site during a surgical procedure. As an example, the solid agent in the form of particles can be delivered by syringe and needle to the target site. As a further example, the solid agent in the form of a coil or stent can be placed manually at the target site during the surgical procedure.

As used herein, thrombus refers to any semi-solid aggregate of blood cells enmeshed in fibrin and clumps of platelets originating from platelets actively binding to the solid-phase agent. In accordance with the invention, a thrombus is formed as a direct result of activated platelet accumulation at the pre-determined site. Thrombosis refers to the formation of a thrombus, typically within a blood vessel. Thrombogenic refers to substances that tend to cause thrombosis, or are thrombus forming.

As used herein, embolus refers to an intravascular mass, which travels through the bloodstream, and through size constraints eventually becomes lodged in a blood vessel or capillary, distal from the site of origin of the intravascular mass. Embolization does not imply an active process, but instead refers to a passive process whereby occlusion of blood vessels occurs by intravascular masses traveling through the blood stream where they become lodged in small blood vessels and capillaries.

In contrast, the present invention involves the delivery of solid-phase material to target vasculature whereupon platelets are actively recruited to the solid-phase surface through the use of a platelet-binding agent. In contrast to embolizing materials described in cited patents, included herein as reference, the agents of the present invention must be delivered in close proximity to the target vasculature due to rapid accumulation of platelets about the solid-phase material.

The present invention improves upon existing methods of producing vascular occlusion by securing platelets to the surface of a solid-phase material through the use of a platelet-binding agent, thereby increasing the effective size of the solid-phase material. For example, a particle (e.g. polylactide, polyglycolide or polylactide-co-glycolide) coated with or containing collagen, which is injected into the blood stream, would rapidly accumulate platelets on its surface, in effect producing an 'onion-effect' of layered, activated platelets in close proximity to the injection site. Therefore the present invention enables delivery of a minimum number of small particles into the bloodstream, whereupon the particles rapidly grow in size from the accretion of platelets actively binding to the platelet-binding agent on or within the particle. Furthermore, the particle-bound platelets would interact with each other thereby forming aggregates of increasing size producing a tight matrix and effecting occlusion of the target vasculature.

The present invention further improves upon existing methods of producing vascular occlusion by securing platelets to the surface of a solid-phase material by means of a platelet-binding agent. The agent of the invention would therefore have the following effects in vivo: a) molding to the contours of the blood vessel or capillary in which it resides, b) producing a solid, impermeable three-dimensional matrix; this in turn produces a tight, impermeable seal within the vessel, thereby maximally inhibiting the delivery of blood to downstream blood vessels and tissues.

For example, the introduction of a platelet-binding particle into the blood stream would proceed through the following sequence of events: a) a single layer of platelets would form on the surface of the particle thereby forming (i) a particle of increased diameter and (ii) a particle coated with activated platelets with the propensity to bind and activate nearby platelets in suspension, herein defined as 'single-layered surface activated platelets' particle (S-SAP particle), b) platelets flowing in the blood stream would interact with platelets bound to the S-SAP particle forming 'onion-like' layers, herein defined as 'multi-layered surface activated platelet particle (M-SAP particle), c) M-SAP would interact with each other through platelet/platelet interaction forming larger aggregates, herein defined as the 'M-SAP matrix'.

As a further example, the introduction of the amorphous platelet binding particle polylactide, polyglycolide or polylactide-co-glycolide particles coated with mammalian collagen into the blood stream would proceed through the following sequence of events: a) single platelets would bind on and within the matrix of the particle thereby forming (i) a particle with increased diameter and rigidity, (ii) a particle coated with and containing activated platelets with the propensity to bind and activate nearby platelets in suspension; b) platelets flowing in the blood stream would interact with the platelets bound to and/or bound within the particle thereby forming aggregates within and/or on the particle, c) particles containing and/or having surface bound platelets would interact with each other to form large particle aggregates.

As used herein, therapeutically beneficial, providing a therapeutic benefit or the like refers to a desirable change in the physiology of the recipient animal. In a preferred embodiment of the invention, the change is detectable. In accordance with the invention, any biological mechanism that involves activated platelets or platelet modulation may be used or harnessed to achieve a beneficial therapeutic result. Exemplary therapeutic benefits produced in accordance with the present invention include, but are not limited to, forming a thrombus, forming a platelet-mediated occlusion, eliminating a hyperplastic tissue or cells, eliminating a tumor and/or tumor cells, diminishing the size of a hyperplastic tissue, diminishing the size of a tumor, causing the hyperplastic tissue or tumor to become susceptible to additional therapies such as chemotherapy and/or radiation therapy or the like, starving or reducing the nutrient supply to a hyperplastic tissue or cancer, repairing AV-malformations, reducing or preventing blood loss from endoleaks and repairing vessel aneurysms.

As used herein, "administering" refers to any action that results in delivering a composition containing a solid-phase agent to a pre-determined cell, cells, or tissue, typically mammalian. Administering may be conducted in vivo, in vitro, or ex vivo. For example, a composition may be administered by injection or through an endoscope or catheter. Administering also includes the direct application to cells of a composition according to the present invention. For example, during the course of surgery, the vasculature of tumor or hyperplastic tissue may be exposed. In accordance with an embodiment of the invention, the exposed cells or vasculature may be exposed directly to a composition of the present invention, e.g., by washing or irrigating the surgical site, vasculature, and/or the cells.

The solid-phase platelet-binding agent can be localized to a specific target site using a binding or targeting agent. Exemplary binding or targeting agents include, but are not limited to: monoclonal antibodies; polyclonal antibodies; chimeric monoclonal antibodies; humanized antibodies; genetically engineered antibodies; fragments of antibodies, selected from the group consisting of F(ab)2, F(ab')2, Fab, F(ab'), Dab, Fv, sFv, scFv, Fc, and minimal recognition unit; single chains representing the reactive portion of monoclonal antibodies (SC-Mab); tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; a ligand (paired with its complementary anti-ligand); oligonucleotides; any of the above joined to a molecule that mediates an effector function; and mimics or fragments of any of the above. Analogs of the above-listed targeting moieties that retain the capacity to bind to a defined target cell population may also be used within the claimed invention. In addition, synthetic targeting moieties may be designed.

Monoclonal antibodies useful in the practice of the present invention include whole antibodies and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins, which employ sequences from more than one species. See, generally, Kohler and Milstein, Nature, 256:495-97, 1975; Eur. J. Immunol., 6:511-19, 1976. The preferred binding and/or targeting agent capable of localizing the solid-phase agent to a target site is an antibody or antibody-like molecule, preferably a monoclonal antibody. A more preferred binding agent is an antibody that binds a ligand/receptor complex on hyperplastic tissue or cells (e.g., tumor) or the vasculature associated with hyperplastic tissue or cells. The most preferred binding agent is an antibody or antibody-like molecule that binds a growth factor/growth factor receptor complex either on or in the vicinity of the tumor mass such as the tumor vasculature. In a preferred embodiment of the invention, the binding agent (i.e., antibody or antibody-like molecules) would bind to the VEGF/VEGF receptor complex. In a further preferred embodiment of the invention, the antibody or antibody-like molecule binding would recognize a neo-epitope (cryptic or previously unavailable epitope) formed due to ligand/receptor (i.e., growth factor/growth factor receptor) interaction. In a further preferred embodiment of the invention, the binding of the antibody or antibody-like molecules to the growth factor/growth factor receptor complex would not affect the function of either the growth factor or the growth factor receptor.

Oligonucleotides, e.g., anti-sense oligonucleotides that are complementary to portions of target cell nucleic acids (DNA or RNA), are also useful as targeting moieties in the practice of the present invention. Oligonucleotides binding to cell surfaces are also useful.

Functional equivalents of the aforementioned molecules are also useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, such minimal polypeptides exhibiting the binding affinity of the targeting moiety.

The Fv fragments of immunoglobulins have many significant advantages over whole immunoglobulins for the purpose of targeted tumor therapy, including better lesion penetration on solid tumor tissue and more rapid blood clearance, as well as potentially lower Fc-mediated immunogenicity. An exemplary single-chain Fv (scFv) binding agent may be engineered from the genes isolated from the variable regions of antibodies recognizing a ligand/receptor complex.

An embodiment of the invention involves a targeting agent having a binding affinity for a marker found, expressed, accessible to binding, or otherwise localized on the cell surfaces of tumor-associated vascular endothelial cells as compared to normal non-tumor-associated vasculature. Further, certain markers for which a targeting agent has a binding affinity may be associated with components of the tumor-associated vasculature rather than on the tumor-associated endothelial cells, themselves. For example, such markers may be located on basement membranes or tumor-associated connective tissue.

It may be desirable to prepare and employ an antibody or other binding agent or moiety having a relatively high degree of selectivity for tumor vasculature, together with little or no reactivity with the cell surface of normal endothelial cells as assessed by immunostaining of tissue sections. It may also be desirable to prepare and employ an antibody or other binding agent or moiety capable of binding an epitope common to all vasculature.

Any composition that includes a solid-phase platelet-binding agent with or without a targeting agent according to the invention may be used to initiate an in vivo therapeutic benefit, thrombus formation, and/or cell killing or regression. The composition may include one or more adjuvants, one or more carriers, one or more excipients, one or more stabilizers, one or more permeating agents (e.g., agents that modulated movement across a cell membrane), one or more imaging reagents, one or more effectors; and/or physiologically-acceptable saline and buffers. Generally, adjuvants are substances mixed with an immunogen in order to elicit a more marked immune response. The composition may also include pharmaceutically acceptable carriers. Pharmaceutically acceptable carriers include, but are not limited to, saline, sterile water, phosphate buffered saline, and the like. Other buffering agents, dispersing agents, and inert non-toxic substances suitable for delivery to a patient may be included in the compositions of the present invention. The compositions may be solutions suitable for administration, and are typically sterile, non-pyrogenic and free of undesirable particulate matter. The compositions may be sterilized by conventional sterilization techniques.

In a preferred embodiment of the invention, a suitable composition includes a binding or targeting agent that binds to ligand/receptor complex. Exemplary antigens useful as targets in accordance with the present invention include, but are not limited to, antigens associated with cancer, including, lung, colon, rectum, breast, ovary, prostate gland, head, neck, bone, immune system, blood, or any other anatomical location. Exemplary antigens and/or pre-determined sites include but are not limited to VEGF/VEGF receptor complex, FGF/FGF receptor complex, or TGF.beta/TGF.beta receptor complex, p-selectin, sialyl-lewis X, endothelin, endothelin receptor, endothelin/endothelin receptor complex, alpha-fetoprotein, platelet-endothelial cell adhesion molecule (PECAM), CD31, CD34, CD36, glycoprotein Ib (GPIb), endoglin, thrombomodulin, endothelial leukocyte adhesion molecule (ELAM), intercellular adhesion molecule 1 (ICAM-1), MHC-I, and MHC-II. The subject may be a human or animal subject.

As noted above, a composition or method of the present invention includes a platelet binding agent or component. In the present invention the preferred platelet binding agent is collagen.

As noted above, a composition or method of the present invention may include a platelet-mediated occlusion enhancer. The platelet-mediated occlusion enhancer may be a moiety that forms a portion of a bi-functional molecule as noted above, may be an ingredient in a composition according to the invention, and/or may be administered separately from a composition according to the invention.

Exemplary platelet-mediated occlusion enhancers include but are not limited to ristocetin, thrombin, heparin-induced thrombocytopenia (HIT) antibodies or portions thereof, antiphospholipid antibodies (APA) or portions thereof, whole antibody molecules via an Fc-mediated mechanism, anti-LIBS antibodies, anti-CD9 antibodies, epinephrine, thrombin receptor activating peptide (TRAP), proteinase-activated receptor (also known as protease activated receptor, PAR) agonists, cathepsin G, elastase, arachidonate, platelet activating factor (PAF), thromboxane A2 (TxA2), TxA2 mimetics, phospholipase A2 (PLA2), activators of protein kinase C (PKC), adenosine diphosphate (ADP), inducers of cyclo-oxygenase 1 (COX-1), inducers of cyclo-oxygenase 2 (COX-2), collagen, von Willebrand factor (VWF), matrix metalloproteinases (MMPs), heparin, heparan sulfate, chondroitin sulfate, ionophores, complement cascade components (e.g., C5b-9) platelet microparticles, platelet membrane fractions.

As noted above, a composition or method of the present invention may include a platelet-mediated occlusion retarder or the like. The platelet-mediated occlusion retarder may be a moiety that forms a portion of a bi-functional molecule as noted above, may be an ingredient in a composition according to the invention, and/or may be administered separately from a composition according to the invention.

Exemplary platelet-mediated occlusion retarders include but are not limited to aspirin, ibuprofen, acetaminophen, ketoprofen, ticlopidine, clopidogrel, indomethacin, dipyridamole, omega-3 fatty acids, prostacyclin, nitric oxide, inducers of nitric oxide, inducers of nitric oxide synthase, matrix metalloproteinase inhibitors (MMPIs, TIMPs), anti-GPIIb/IIIa agents, anti-□v□3 agents, anti-□2□1 agents, anti-CD36 agents, anti-GPVI agents, aurintricarboxylic acid, thrombin receptor antagonists, thromboxane receptor antagonists, streptokinase, urokinase, tissue plasminogen activator (tPA).

In addition, it is known that platelets that have been cooled below their membrane phase transition temperature (i.e., <15 degrees C.) become irreversibly activated. Although the platelets function normally if transfused into a patient, the platelets are rapidly cleared from the body (i.e., in approximately 24 hours, in contrast to normal circulating platelet life span of 7 to 10 days). Although these platelets are cleared rapidly, they bind with high avidity to PGLA/Collagen. Therefore, transfusion of cooled platelets provides an additional means to enhance thrombus formation at the target site. Therefore, one embodiment of the invention includes controlling platelet-mediated occlusion by administering platelets cooled as noted above.

As noted above, the targeting moiety may be, or may be bound to, one member of a binding pair. Methods according to the invention may require a time period sufficient for accumulation of the targeting moiety at the site of localization, for optimal target to non-target accumulation, for accumulation and binding of the second member of the binding pair, and/or for clearance of unbound substances.

In accordance with the invention, two, three or more step targeting or localization steps may be used. Many of these protocols are well known in the art (see, for example, U.S. Pat. No. 5,578,287 using a biotin/avidin protocol). Exemplary multiple step protocols include, but are not limited to, administering a binding agent-ligand, administering an anti-ligand to clear unbound binding agent and to localize bound binding agent-ligand, and administering an active agent-ligand. As used herein, active agent refers to any therapeutic agent that is active or becomes active and leads to a therapeutic benefit.

In accordance with a method of the invention, the binding agent must be capable of binding a ligand/receptor complex, and may be administered to the patient by any immunologically suitable route. For example, the binding agent may be introduced into the patient by an intravenous, intra-arterial, subcutaneous, intraperitoneal, intrathecal, intravesical, intradermal, intramuscular, or intralymphatic route. The composition may be in solid, solution, tablet, aerosol, or multi-phase formulation forms. Liposomes, long-circulating liposomes, immunoliposomes, biodegradable microspheres, micelles, or the like may also be used as a carrier, vehicle, or delivery system. Further more, using ex vivo procedures well known in the art, blood, plasma or serum may be removed from the patient; optionally, it may be desirable to purify the antigen in the patient's blood; the blood or serum may then be mixed with a composition that includes a binding agent or the solid-phase agent according to the invention; and the treated blood or serum is returned to the patient. The clinician may compare the responses associated with these different routes in determining the most effective route of administration. The invention should not be limited to any particular method of introducing the binding agent into the patient.

Administration may be once, more than once, or over a prolonged period. As the compositions of this invention may be used for patients in a serious disease state, i.e., life-threatening or potentially life-threatening, excesses of the solid-phase agent may be administered if desirable. Actual methods and protocols for administering pharmaceutical compositions, including dilution techniques for injections of the present compositions, are well known or will be apparent to one skilled in the art. Some of these methods and protocols are described in Remington's Pharmaceutical Science, Mack Publishing Co. (1982).

A solid-phase agent may be administered in combination with other binding agents, or may be administered in combination with other treatment protocols or agents, e.g., chemotherapeutic agents, embolizing agents such as Gelfoam or polyvinyl alcohol (PVA) particles or the like.

As is well known in the art, a disadvantage associated with administering treatment agents or treatment agent conjugates in vivo includes non-target or undesirable target binding. It is therefore a desirable attribute of any administered composition to minimize non-target binding, to minimize non-target exposure to the treatment agent or active agent, and/or to maximize clearance of non-bound binding agent, ligand, or active agent. Moreover, optimizing these attributes typically permits administering a higher dose of active agent, a therapeutic agent, or an element of the process that activates a previously un-activated agent. Those skilled in the art are well versed in selecting the optimal parameters for administering the highest possible dose while remaining safely below a toxic threshold.

In accordance with a preferred embodiment of the invention, therefore, un-activated platelets accumulate or are induced to accumulate at a pre-determined site through binding to the solid-phase agent, and then the properly localized platelets are selectively activated.

In accordance with a preferred embodiment of the invention, activated platelets accumulate or are induced to accumulate at a pre-determined site through binding to the solid-phase agent or through platelets bound to the solid-phase agent.

The effectiveness of the present invention may be monitored by conventional assays that determine thrombus formation, morphometric studies of thrombus formation, tumor necrosis, tumor size, tumor morphology, and/or thrombus formation that results in tumor necrosis, blood flow studies (e.g., angiography, Doppler ultrasound, radiography, CT scan, MRI), or reduction in pain symptoms. One skilled in the art will recognize that other tests may be performed to assess or monitor therapeutic benefit.

It will be recognized by those skilled in the art that for certain congenital and pathological conditions, some of which are listed below, it is desirable to modify a composition or method of the present invention to compensate for a pre-disposition of the patient to bleed excessively or to thrombose. Under these circumstances, use of modifying agents, which either enhance or dampen a method or composition of the invention, can be employed. The use of these modifying agents is predicted to minimize bleeding or clotting episodes. Moreover, the use of modifying agents enables controlled administration of a composition according to the invention under normal circumstances (i.e., normal hemostasis).

Exemplary pro-thrombotic or pro-coagulant conditions that may warrant the using of controllers, retarders, or agents that diminish a method or composition of the invention include, but are not limited to, Factor $V^{Leiden}$ deficiency, antiphospholipid syndrome (APS), Protein C and/or Protein S and/or Antithrombin III deficiency, deep vein thrombosis (DVT), pseudo-von Willebrands disease, Type IIb von Willebrands disease, peripheral vascular disease (PVD), and high blood pressure, among others. Exemplary conditions that include a risk of hemorrhage that may warrant using enhancers or agents that augment a method or composition of the invention include but are not limited to, any condition that includes a risk of hemorrhage, including but not limited to coagulation factor deficiencies, hemophilia, thrombocytopenia, and anticoagulation therapy, among others. Controlling thrombus generation includes at least one of altering the temperature at the pre-determined site, altering the rate of blood flow at the pre-determined site, and altering the blood pressure at the pre-determined site.

As an example of the foregoing, it will be recognized by those skilled in the art that upon initiation of the vascular occlusion process, reversal or dampening of the associated prothrombotic condition may be necessary. In such cases, administration of agents that reduce platelet reactivity will, in turn, reduce response to the vascular occlusion initiators. Such agents are readily known by those skilled in the art and include, but are not limited to: aspirin or aspirin-like compounds, ibuprofen, acetaminophen, ketoprofen, ticlopidine, clopidogrel, indomethacin, omega-3 fatty acids, prostacyclin, nitric oxide, inducers of nitric oxide, inducers of nitric oxide synthase, matrix metalloproteinase inhibitors (MMPIs, TIMPs), anti-GPIb agents, anti-GPIIb/IIIa agents, anti-$\alpha v \beta 3$ agents, anti-$\alpha 2 \beta 1$ agents, anti-CD36 agents, aurintricarboxylic acid, thrombin receptor antagonists, thromboxane receptor antagonists, streptokinase, urokinase, tissue plasminogen activator (tPA).

An exemplary process in which it may be desirable to enhance or augment platelet occlusion process includes thrombocytopenic (low platelet count) patients. These individuals would benefit from concomitant or pre-administration (transfusion) of platelet products to provide an adequate resource of platelets to accomplish platelet occlusion. It will be recognized by those skilled in the art that all transfusable products mimicking or approximating normal platelet function can be used under such circumstances. Such agents include but are not limited to: random donor platelets, apheresis platelets, autologous platelets, washed platelets, platelet membrane fractions, cooled platelets, frozen platelets, particles containing or expressing platelet membrane components, platelet substitutes and whole blood.

As a further example, specific platelet-function enhancing agents can be employed to boost or enhance initial platelet reactivity once targeted to the site of therapy. Agents known to those skilled in the art have been demonstrated to enhance existing platelet reactivity and/or lower the threshold limiting sufficient platelet reactivity to facilitate irreversible platelet adhesion and/or platelet degranulation and/or platelet/platelet binding and/or platelet accretion about an existing thrombus. These agents include but are not limited to: ristocetin, thrombin, heparin-induced thrombocytopenia (HIT) antibodies or portions thereof, antiphospholipid antibodies (APA) or portions thereof, whole antibody molecules via an Fc-mediated mechanism, anti-ligand-induced binding site (anti-LIBS) antibodies or portions thereof, anti-CD9 antibodies or portions thereof, epinephrine, thrombin receptor activating peptide (TRAP), PAR agonists, cathepsin G, elastase, arachidonate, thromboxane A2 (TxA2) mimetics, TxA2, phospholipase A2 (PLA2), activators of protein kinase C (PKC), adenosine diphosphate (ADP), collagen, von Willebrand factor (VWF), matrix metalloproteinases (MMPs), heparin, heparan sulfate, chondroitin sulfate, ionophores, platelet microparticles, platelet membrane fractions.

Once introduced into the bloodstream of an animal bearing a tumor, hyperplastic tissue, AV-malformation, aneurysm or endoleak, the solid-phase agent will localize in the target vasculature; bind or immobilize platelets, whereby immobilization activates the platelets; and the activated platelets in turn bind and activate other platelets until an occlusion is formed. Platelet activation and binding facilitates leukocyte binding to the activated platelets further enhancing occlusion of the target vasculature.

EXAMPLES

Example 1

The technique of preparing monoclonal antibodies against antigenic cell surface markers is quite straightforward and may be readily carried out using techniques well known to those of skill in the art as exemplified by the technique of Kohler and Milstein (1975). Generally speaking, the preparation of monoclonal antibodies using stimulated endothelial cells involves the following procedures. Cells or cell lines derived from human tumors are grown in tissue culture for four or more days. The tissue culture supernatant ("tumor-conditioned medium") is removed from the tumor cell cultures and added to cultures of human umbilical vein endothelial cells (HUVEC) at a final concentration of 50% (v/v). After 2 days culture, the HUVEC are harvested non-enzymatically and 1-2×$10^6$ cells injected intraperitoneally into mice. This process is repeated three times at two-week intervals, the final immunization being by the intravenous route. Three days later, the spleen cells are harvested and fused with SP2/0 myeloma cells by standard protocols (Kohler and Milstein, 1975). Hybridomas producing antibodies with the appropriate reactivity are cloned by limiting dilution.

From the resultant collection of hybridomas, one will select one or more hybridomas that produce an antibody that recognizes the activated vascular endothelium to a greater extent than it recognizes non-activated vascular endothelium. The ultimate goal is the identification of antibodies having virtually no binding affinity for normal endothelium. Suitable antibody-producing hybridomas are identified by screening using, for example, an ELISA, RIA, IRMA, IEF, or similar immunoassay against one or more types of tumor-activated endothelial cells. Once candidates have been identified, one will test for the absence of reactivity against non-activated or "normal" endothelium or other normal tissue or cell types. In this manner, hybridomas producing antibodies having an undesirably high level of normal cross-reactivity for the particular application envisioned may be excluded.

Example 2

The technique of preparing single chain antibodies that specifically recognize a ligand/receptor complex, specifically a growth factor/growth factor receptor complex is employed, whereby the resulting antibody molecules recognize the growth factor/growth factor receptor complex, but do not bind to either the growth factor or growth factor receptor alone. These antibodies can be formed through the immunization of mice with a complex of purified ligand and receptor, such as VEGF and VEGF receptor, and the resulting V genes used to construct an antibody library in filamentous phage. The phage display of antibody fragments allows the production of recombinant antibody molecules against activated endothelial cell antigens, specifically a ligand/receptor complex. The phage system mimics the vertebrate immune system.

Female BALB/c mice are immunized with HPLC-purified recombinant VEGF and VEGF receptor (soluble VEGF/FLT-1 receptor or VEGF/KDR receptor, as examples) in complex in the presence of an adjuvant such as Quil A. After the appropriate antibody titre is reached (usually following the fourth boost), the mice are sacrificed and the spleens isolated. Messenger RNA (mRNA) is isolated from the spleen and transcribed to cDNA. The V genes of the cDNA are amplified and assembled as "single chain Fv" (scFv). After digestion with the appropriate restriction enzymes, the scFv are ligated into phagemid vectors. Competent *E. coli* cells are then transformed with these phagemid libraries, and after infection with helper phage (e.g., M13K07, Pharmacia), phage particles displaying the scFv are prepared. Selected clones are screened for expression of soluble scFv binding to the ligand/receptor complex, but do not bind to either the ligand alone or the receptor alone. This screening is accomplished using standard ELISA techniques, with the ligand/receptor complex, ligand and receptor used as solid-phase antigens, respectively.

Example 3

A variety of endothelial cell markers are known that can be employed as existing or inducible targets for the practice of this aspect of the invention including VEGF/VPF (vascular endothelial growth factor/vascular permeability factor), endothelial-leukocyte adhesion molecule (ELAM-1; Bevilacqua et al., 1987); vascular cell adhesion molecule-1 (VCAM-1; Dustin et al; 1986) intercellular adhesion molecule-1 (ICAM-1; Osborn et al., 1989); the agent leukocyte adhesion molecule-1 (LAM-1 agent) or even a major histocompatibility complex (MHC) Class II antigen, such as HLA-DR, HLA-DP, or HLA-DQ (Collins et al., 1984). Of these, the targeting of the VEGF/VEGF receptor complex will likely be preferred. Monoclonal antibodies or specific peptides recognizing the above endothelial cell antigens can be bound to the solid-phase agent, such as particles coated with VWF, and delivered to target vasculature by means of a catheter or similar delivery device. The particles are thereby bound to the endothelial cells in the target vasculature leading to platelet binding and platelet activation on the particle, which in turn leads to platelet aggregation about the particle and eventually thrombus formation. The formed thrombus occludes the targeted vasculature thereby preventing delivery of oxygen and nutrients to the down-stream tissue.

Example 4

Targeting platelets to a specific site may take the form of platelets binding directly to the solid-phase agent through interaction VWF immobilized on the solid-phase agent. For example, recombinant and/or human and/or porcine VWF immobilized on a particle of an approximate diameter of 1 μm to 5 mm can be delivered to a target site by various means, such as by catheter. Platelet binding can take place after delivery of the VWF-particle to the target vasculature whereby platelets flowing in the blood stream contact the particles, bind to the particles, spread across the particles, activate, bind other platelets and eventually form a thrombus that occludes the blood vessel. Platelet binding to the VWF-particle can also be initiated ex vivo, whereby the platelets contact the particles in a vessel outside the body, and are subsequently delivered to the target site by means of a catheter or similar agent delivery device. Particle size is selected such that upon initiation of platelet reactivity with the particles (i.e., platelet binding to the particles) progression of the particle beyond the capillary bed cannot occur due to size limitations or because of the particle-associated platelets and/or bound coagulation proteins interacting with the vessel wall receptors. VWF particle sizes, therefore, could range from about 1 μm to about 5 mm in diameter. Most preferably the particles will range between 5 μm and 2 mm in diameter. An even more preferable diameter of the particle would be between 20 μm and 300 μm.

Example 5

Particles

Particles of various compositions can be used as solid-phase agents for the purpose of the present invention. The following particles have been tested for their ability to bind agents that bind platelets. Polystyrene microspheres were purchased from Polysciences Inc., (Warrington, Pa.) and coated with human von Willebrand factor through a passive adhesion process (incubation in 0.2M carbonate buffer, pH 9.0-9.6) or through a covalent linkage to derivatized beads using carbodiimide or glutaraldehyde. Several types of beads were tested including plain polystyrene microspheres (cat. # 07310, 17134, 17135, 07312, 07313, 07314), polybead amino microspheres (cat. # 19118), polybead carboxylate microspheres (cat. # 17141), fluoresbrite microspheres (cat. # 17155, 17156), polystyrene dyed microspheres (cat. # 15715, 15714, 15716), and paramagnetic particles (cat. # 19829). All beads bound von Willebrand factor, and upon subsequent testing bound platelets. Binding of platelets to the beads was confirmed by aggregometry and phase contrast microscopy.

Other particles tested included polyvinyl alcohol (PVA) particles (Cook, Bloomington, Ind.) and macro-aggregated albumin (MAA) particles (Edmonton Radiopharmaceutical Centre, Edmonton, Alberta, Canada). In separate experiments, von Willebrand factor was bound passively (carbonate buffer, as above) and covalently (glutaraldehyde linkage, as above) to the particles. Binding of platelets to the particles was then confirmed using aggregometry, phase contrast microscopy and fluorescence microscopy (anti-CD61 antibody labeled with FITC).

Example 6

Comparison of Mammalian VWFs

Porcine VWF, bovine VWF, and human VWF were immobilized on polystyrene particles using two approaches. The first approach (direct binding) employed passive adsorption of the material to the solid-phase particle in the presence of 0.2M carbonate (pH 9.35). The second approach (indirect binding) consisted of the isolation of VWF from porcine, bovine, and human plasmas, respectively, using an anti-VWF antibody that had been immobilized on the surface of the solid-phase particle. In the latter approach, the antibody (rabbit source) used was purchased from Dako (Mississauga, Ontario; cat # A0082), and as per information provided by the manufacturer, was confirmed to bind human, bovine and porcine von Willebrand factor. The antibody was fixed to polystyrene beads (4.5 μm in diameter) by passive adsorption in carbonate buffer (0.2M, pH 9.35) and incubated with the respective source plasmas for 60 minutes at room temperature. The beads were washed free of unbound protein and used to challenge whole blood and platelet rich plasma from humans and pigs. In a like manner, human, porcine and bovine VWFs were individually bound directly to the beads (i.e. without a linking antibody) by passive adsorption as outlined above, and used to challenge human and porcine platelets (whole blood and platelet rich plasma [PRP]). In some experiments, porcine and human PRP were mixed together and challenged with the various agents (see below).

| Immobilized VWF | | | | | |
|---|---|---|---|---|---|
| Direct | Ab Capture | Source VWF | Whole Blood | PRP | 50:50 PRP (human:porcine) |
| ✓ | — | Human | Human ++++ Porcine + | Human ++++ Porcine + | +++++ |
| — | ✓ | Human | Human ++++ Porcine + | Human ++++ Porcine + | +++++ |

-continued

| Immobilized VWF | | | | | |
|---|---|---|---|---|---|
| Direct | Ab Capture | Source VWF | Whole Blood | PRP | 50:50 PRP (human:porcine) |
| ✓ | — | Porcine | Human +++++ Porcine +++ | Human +++++ Porcine +++ | +++++ |
| — | ✓ | Porcine | Human +++++ Porcine +++ | Human +++++ Porcine +++ | +++++ |
| ✓ | — | Bovine | Human + Porcine + | Human + Porcine + | + |
| | | Bovine | Human + Porcine + | Human + Porcine + | + |

+ weak platelet reaction,
++ moderately weak platelet reaction,
+++ moderate platelet reaction,
++++ strong platelet reaction,
+++++ very strong platelet reaction Example 7

White Cell Interaction

Particles bound with porcine or human VWF characteristically bound human or porcine platelets, depending on the source blood. In addition, white cells including monocytes, granulocytes and lymphocytes were observed to interact with the platelets bound to the particles (confirmed by differential staining and microscopic examination).

Platelet activation at the target site induces secondary effects that may enhance diminution or killing of the target tissue. Release of agents by the activated platelets such as platelet factor 4 (PF4) inhibit angiogenesis. Post activation platelet release of chemoattractants such as RANTES enhance the effects of leukocytes (e.g., eosinophils, monocytes) on target tissue. Post activation expression by the platelets of granular constituents such as CD62 will induce binding of monocytes and polymorphonuclear leukocytes (PMNs) resulting in tissue factor expression (monocyte; procoagulant) and cellular activation and attack (PMNs). In addition, release of CD40 ligand (CD40L) by activated platelets at the target site induces tissue factor expression by monocytes leading to a local hyper-coagulable state.

Example 8

The solid-phase agent can also take the form of a coil or a stent. VWF of recombinant or mammalian origin can be bound to these solid phase agents and delivered to the target vasculature by various means including surgery and/or by catheter. The target site, such as an aneurysm, can be reached through the blood stream using specific catheters and associated guide wires. A guide wire is introduced into the vascular system through an entry site such as the femoral artery and gently pushed through the major blood vessels to the target site. The catheter is introduced over the guide wire to the target site, whereupon the guide wire is removed. The solid-phase platelet-binding coil is then pushed through the lumen of the catheter to the aneurysm where it is deployed. VWF bound to the coil specifically binds platelets flowing in the bloodstream. The platelets activate and accumulate about the coil rapidly, thereby forming a localized stationary thrombus, in turn reducing the risk of aneurismal rupture.

Example 9

Acute Effects of Particle-Immobilized VWF in a Porcine Model

The study was designed to evaluate the effectiveness of particles coated with human VWF in inducing thrombus formation in the vasculature of the pig kidney. In this procedure, the renal artery was catheterized using a 20-22 gauge angiocatheter. The renal vessels were exposed by surgery and a Doppler flow probe attached to the renal vessels to monitor blood flowing into and out of the target organ. No noticeable difference was seen between flow readings taken from the renal artery and vein; therefore, all readings were further taken from the renal vein to be indicative of blood flow through the target kidney. Human VWF was covalently bound to human MAA by overnight incubation with glutaraldehyde. Previous titration studies varying the amount of VWF bound to MAA on a per weight protein basis had established that ratios of 1:5 through 1:80 (MAA:VWF) provided sufficient immobilized VWF to induce platelet binding and activation. On this basis, a ratio of 1:20 (MAA:VWF) was chosen for in vivo studies. Particle analysis by phase contrast microscopy demonstrated that the particle size in the final preparation ranged from 30 μm through to 250 μm (as estimated by light microscopy using a micrometer/hemacytometer).

Injection of MAA/VWF (500 μl or 1 ml) followed by human PRP (500 μl containing approximately 200—400×10$^6$ platelets) into the renal artery of the pig caused a dramatic decrease in blood flow. Human platelets were injected after the test agent to approximate conditions within a human as closely as possible. In addition, binding of porcine platelets to human VWF was noted to be very weak (see Example 6, above). Within 10 minutes of injection of the test agent, the blood flow had dropped to less than half of baseline levels. Within 15 minutes of injection of the test agent, the blood flow had dropped to less than 20% of the baseline values. Blood flow to the organ did not increase during the 90-minute monitoring period.

Conversely, control agent (MAA alone; identical protein concentration) injected into the renal artery of the contra lateral kidney showed a transient decrease in blood flow. The blood flow decreased by 50% initially, but rapidly returned to near baseline levels, i.e., >80% of original blood flow within 15 minutes and >90% of original blood flow within 30 minutes.

Histological examination of the target vasculature revealed a large thrombus in the immediate branches of the renal artery in the test organ with minor thrombosis of the renal vasculature in the control kidney. No thrombi were noted in the liver, lungs, spleen, brain, heart and eyes of the control or test animals.

Example 10

Chronic Effects of Particle-Immobilized VWF in a Porcine Model

In a manner similar to the procedure outlined in Example 9, the renal arteries of two test and two control pigs were catheterized using 20-22 gauge angiocatheters. A Doppler flow probe was placed surgically on the renal vein of each animal and the lead wires exposed on the outer skin of the animal after closing the initial incision. After establishing a baseline for blood flowing through the affected kidney, 1 ml of MAA: VWF particles (11 g total protein) followed by 1 mL human platelet rich plasma (approximately 460×10$^6$ platelets (platelet count 458×10$^9$/liter) were injected into the renal arteries of the test animals, and an identical amount of MAA was injected into the control animals. The animals were transferred to metabolic crates and monitored at varying time intervals over a 7-day period. The following table presents blood flow results from these studies.

| PORCINE DOPPLER BLOOD FLOW (milliliters per minute) | | | | |
|---|---|---|---|---|
| Day | Test 1 | Control 1 | Test 2 | Control 2 |
| 0 | 28 | 70 | 35 | 35 |
| 1 | 17 | 15 | 11 | 103 |
| 2 | 32 | 24 | 15 | 71 |
| 3 | 3 | 109 | 16 | 85 |
| 4 | 3 | 101 | 17 | 78 |
| 5 | 3 | 140 | 3 | 65 |
| 6 | 1 | 140 | 0 | 55 |
| 7 | 3 | 148 | 2 | 30 |

The major organs and tissues of the control and test animals were examined histologically for evidence of thrombosis and other treatment-associated damage. No thrombosis was observed except in the renal vasculature of the target kidney.

Example 11

MAA/VWF Labeling with Sodium Pertechnetate Tc 99m

MAA/VWF particles were prepared by conjugating human VWF (source Alphanate, Alpha Therapeutics Corp.) to MAA particles (11 mg protein; source MAA for injection, Edmonton Radiopharmaceutical Centre) using glutaraldehyde (0.0625% v/v, final). The protein ratios ranged from 40:1 to 20:1 (MAA:VWF). The functionality of the particles was checked by challenging citrated platelet rich plasma and citrated whole blood from a healthy non-medicated (greater than 2 weeks) volunteer with the MAA/VWF particles with stirring at 500 rpm for 10 minutes (10 μl particles+100 μl platelet source). Observation of the reaction by phase contrast microscopy confirmed the ability of the particles to bind and activate platelets, forming large masses of platelets and MAA/VWF particles.

The MAA/VWF particles were then labeled with sodium pertechnetate Tc 99 m using activities ranging from 88 MBq to 300 MBq. Equal volumes of the particles in saline and sodium pertechnetate Tc 99m were incubated at room temperature for 10 minutes. Labeling efficiency was determined using thin layer chromatography and found to be in excess of 95%.

The Tc 99m labeled MAA/VWF particles were then tested to evaluate the effect of the labeling on the functionality of the particles. Phase contrast microscopy confirmed that the Tc 99m labeled MAA/VWF particles were capable of binding and activating platelets. There was no apparent reduction in the functional activity of the labeled particles.

Example 12

Fluoroscopy Studies of MAA/VWF Thrombosis of Porcine Renal Vasculature

MAA/VWF was delivered to porcine renal vasculature using a femoral artery approach. A 5-Fr sheath catheter was inserted into the femoral artery of 18 to 20 kg piglets after general anesthesia (halothane) and guided by fluoroscopy to the left renal artery. The catheter was positioned such that upon delivery of contrast dye, only the lower pole of the kidney's vasculature was visualized. At time zero 1 ml of MAA/VWF particles (size range 30-250 micron) were delivered slowly (over 10 seconds) to the renal vasculature. Ten (10) seconds later 1 ml human PRP ($420 \times 10^9$ per liter) was delivered and the catheter flushed with 1 ml saline. The catheter was kept in place and after a twenty (20) minute waiting period contrast agent was again delivered to the target vasculature. The contrast agent was observed to pool at the end of the catheter then move rapidly into the vasculature of the upper pole of the kidney. The vasculature of the lower pole of the kidney slowly accumulated contrast agent that did not dissipate (greater than 20 minutes), while the upper pole vasculature rapidly lost the contrast agent (less than 5 seconds). With the animal under anesthetic and the catheter still in place, the affected kidney was surgically exposed, the renal vasculature clamped just proximal to the catheter and the affected kidney removed. The renal artery was opened through a longitudinal incision and dissected toward the kidney. A large thrombus was noted distal to the tip of the catheter extending deep within the vasculature of the lower pole of the kidney. No clotting was noted in the vasculature of the upper pole of the kidney. In addition, the lower pole of the affected kidney was noticeably blanched indicating a lack of blood flow, while the upper pole of the kidney exhibited normal red coloration.

In a separate experiment following the above outlined procedure the catheter was directed to the vasculature of the lower pole of the target kidney and used to deliver 1 ml of MAA/VWF particles followed by 1 ml of human PRP. After 20 minutes blood flow to the lower pole of the kidney was notably impeded as determined by fluoroscopy. As before, the contrast dye moved rapidly into the upper pole vasculature after pooling at the tip of the catheter. The catheter was then repositioned and MAA/VWF followed by human PRP was delivered to the upper pole vasculature. After a 20 minute waiting period contrast dye was again injected. Fluoroscopy revealed that blood flow to the upper pole vasculature was blocked. The contrast dye did not enter the lower pole vasculature. The target kidney with associated renal vessels was then removed surgically prior to sacrificing the animal. Immediate dissection of the kidney revealed extensive thrombosis of the blood vessels in both the upper and lower poles of the kidney.

Example 13

Preparation of Collagen-coated Particles

Various sources of collagen were bound to different particle types by passive adsorption, or chemical conjugation.

Collagen derived from calf-skin and bovine tendon (Sigma; St Louis, Mo.), was bound to 4.5 µm diameter polystyrene particles (Polybead; Polysciences Corp.; Warrington, Pa.) through passive adsorption by overnight incubation in the presence of mild acid. The particles were washed free of unbound collagen by centrifugation (3 cycles; saline, 0.15 M) and left suspended in saline. The particles were stored at 4° C. until needed.

Collagen purchased from Bard Inc. as Avitene flour (Bard; Murray Hill, N.J.) was solubilized in mild acid and covalently bound to 100 µm diameter polylactic acid (PLA) particles (G. Kisker, Germany) using EDC (Sigma) as a linking agent (3 hrs, 22° C.). Acid-solubilized Avitene was covalently bound to 100-135 µm diameter polylactide-co-glycolide (PLGA) particles (PolyMicrospheres; Indianapolis, Ind.), or 240 µm PLGA particles using glutaraldehyde (Fisher Scientific Inc., Edmonton, Canada) as a linking agent. Conjugations were accomplished by overnight incubation using glutaraldehyde. The particles were washed free of unbound collagen, blocked with 1% (w/v) bovine serum albumin (BSA) and left suspended in PBS. The particles were stored at 4° C. until needed.

Example 14

Detection of Collagen Bound to Particles

Collagen bound to the various particle types was detected using a collagen-specific monoclonal antibody. Particles were incubated with saturating concentrations of anti-collagen IgG (Sigma) for 1 hour at 22° C. After washing away unbound antibody, the particles were incubated with saturating amounts of goat anti-mouse IgG-FITC for 1 hour at 22° C. (Sigma). After washing away unbound antibody, the particles were observed by fluorescence microscopy. Bovine serum albumin (BSA) coated particles served as negative control.

Example 15

Collagen-coated Particle Mediated Platelet Activation

Collagen coated particles (acid-soluble, fibrillar, Avitene) were mixed with citrated whole blood from healthy non-medicated donors to determine the effect of the particles on platelet activation. Agitation of the reaction mixture was accomplished by mixing on a rotary shaker in microwells. Particle-dependent platelet activation was assessed by phase contrast microscopy and by a platelet counting technique. Mixing collagen-coated particles with whole blood induced platelet activation and binding to the particles. In contrast to the addition of acid soluble collagen (i.e. not particle bound), which caused extensive platelet aggregation observed as platelet clumps in the reaction mixture, the collagen-particle-activated platelets remained localized to the particle surface facilitating particle bound platelet aggregation. Platelet counts post-mixing were significantly less than the starting platelet counts as determined by automated cell counting (Coulter Ac.T; Coulter, Fullerton, Calif.).

Example 16

Inhibition Studies

Citrated whole blood from healthy, unmedicated donors was incubated with saturating concentrations of anti-GPIb antibody, clone AK2 (Biodesign International; Saco, Me.). The whole blood was then challenged with decreasing numbers of collagen-coated polystyrene microspheres. BSA microspheres were used as negative control. The results of the experiments are shown in the table below.

|  | Percent Platelets Remaining After Reaction (100% test agent) | | | Percent Platelets Remaining After Reaction (1:1 dilution of test agent) | | |
|---|---|---|---|---|---|---|
| Agent | Donor 1 | Donor 2 | Donor 3 | Donor 1 | Donor 2 | Donor 3 |
| Collagen Coated Polystyrene Microspheres | 0.93 | 1.1 | 2.39 | 4.97 | 6.29 | 93.99 |
| Collagen Coated Polystyrene Microspheres + Anti GP1b | 1.31 | 5.92 | 34.2 | 23.2 | 75.89 | 100.18 |
| Change in Platelet Reactivity | 1.4-fold decrease | 5.4-fold decrease | 14.3-fold decrease | 4.7-fold decrease | 12.1-fold decrease | 1.1-fold decrease |

Anti-GPIb antibody significantly reduced platelet reactivity with the collagen-coated microspheres indicating that the platelets were activated by an immobilized VWF-dependent mechanism. This result is not surprising since collagen exposed as part of the subendothelium is known to bind circulating VWF, which in turn serves to capture platelets flowing past the area of vascular damage.

In a separate series of experiments, PLGA coated collagen microspheres were used to challenge, whole blood that had been incubated with saturating concentrations of anti-GPIb, collagen particles that had been incubated with anti-collagen antibodies. The results of the experiments are shown in the table below.

| Test Agent | Percent Platelets Remaining After Reaction |
|---|---|
| Collagen Coated PLGA particles | 9.7 |
| Collagen Coated PLGA particles + anti collagen antibody | 90.2 |
| Whole Blood + anti GPIb antibody | 54.6 |

Both the anti-GPIb and the anti-collagen antibodies reduced platelet reactivity with the PLGA/collagen microspheres. The results demonstrate that platelets are activated in the presence of PLGA/collagen microspheres through two mechanisms, a VWF-dependent and a VWF-independent mechanism. Since collagen is required to capture VWF from the whole blood, treating the collagen-coated microspheres with anti-collagen antibody inhibited VWF binding to the collagen. In addition, collagen-dependent platelet activation through other receptor pathways was essentially eliminated. In contrast, inhibiting VWF/platelet interaction by blocking GPIb, had no effect on the collagen-dependent platelet interaction. The results demonstrate that both pathways contribute to PLGA/collagen microsphere-dependent platelet activation. The results also support the use of inhibitors to modulate platelet activation induced by solid-phase platelet binding agents in an in vivo setting.

Although the present invention has been described in terms of particular preferred embodiments, it is not limited to those embodiments. Alternative embodiments, examples, and modifications, which would still be encompassed by the invention, may be made by those skilled in the art, particularly in light of the foregoing teachings.

We claim:

1. A method for treating a vascularized tumor or hyperplastic tissue, comprising administering to a mammal at a pre-determined site at or near a vascularized tumor or hyperplastic tissue, a solid-phase agent comprising a binding agent comprising collagen and being capable of binding platelets, and subsequently inducing a thrombus in vivo comprising:
   binding said collagen to a solid-phase agent;
   capturing platelets by exposing platelets to said collagen, inducing activation of the platelets, and
   allowing a thrombus to form at said pre-determined site, thereby limiting the blood supply at said pre-determined site and treating said vascularized tumor or hyperplastic tissue.

2. The method of claim 1 wherein collagen is bound to a solid phase agent selected from the group consisting of polystyrene beads, polylactic acid particles, polyglycolic acid particles, and polylactide-co-glycolide particles.

3. The method of claim 1 wherein the source of collagen is a mammal.

4. A method of treating a vascularized tumor or hyperplastic tissue comprising administering to a pre-determined site at or near a vascularized tumor or hyperplastic tissue collagen bound to a solid support, allowing the collagen to capture and activate platelets, and allowing the activated platelets to form a thrombus.

5. The method of claim 4 wherein the solid support is selected from the group consisting of polyvinyl alcohol (PVA); polystyrene; polycarbonate; polylactide; polyglycolide; lactide-glycolide copolymers; polycaprolactone; lactide-caprolactone copolymers; polyhydroxybutyrate; poly-alkylcyanoacrylates; polyanhydrides; polyorthoesters, albumin; collagen; gelatin, polysaccharides; dextrans; starches; methyl methacrylate; methacrylic acid; hydroxylalkyl acrylates; hydroxylalkyl methacrylates; methylene glycol dimethacrylate; acrylamide; bisacrylamide; cellulose-based polymers; ethylene glycol polymers and copolymers; oxyethylene and oxypropylene polymers; polyvinyl acetate; polyvinylpyrrolidone and polyvinylpyridine; magnetic particles; fluorescent particles; animal cells; plant cells; macro-aggregated and micro-aggregated albumin; denatured protein aggregates; and liposomes; any of the above used singly or in combination.

6. The method of claim 4 wherein the solid support is selected from polystyrene; polylactide; polyglycolide, lactide-glycolide copolymers, alone or in combination.

7. The method of claim 4 wherein administering comprises administering using a catheter, microcatheter, syringe, by a surgical procedure, or by manual placement.

8. The method of claim 4 further comprising administering an inhibitor that inhibits platelets binding to the collagen.

9. A method of treating a vascularized tumor or hyperplastic tissue comprising administering to a pre-determined site at or near a vascularized tumor or hyperplastic tissue von Willebrand Factor bound to macroaggregated albumin, allowing the von Willebrand Factor to capture and activate platelets, and allowing the activated platelets to form a thrombus.

10. A method of treating a vascularized tumor or hyperplastic tissue comprising administering to a pre-determined site at or near a vascularized tumor or hyperplastic tissue von Willebrand Factor bound to PLGA, allowing the vWF to capture and activate platelets, and allowing the activated platelets to form a thrombus.

11. The method of claim 1 wherein the solid-phase agent is a particle.

12. The method of claim 1 wherein the solid-phase agent is a coil.

13. The method of claim 1 wherein the solid-phase agent is a stent.

14. The method of claim 1 wherein the solid-phase agent includes a targeting moiety.

15. The method of claim 14 wherein the targeting moiety is directed to an antigen on target vasculature.

16. The method of claim 1 wherein the solid-phase agent comprises biotin or avidin or derivatives thereof.

17. The method of claim 15 wherein the targeting moiety comprises biotin, peptides, human Fc fragments, a fusion protein, alone or in combination.

18. The method of claim 11 wherein the particle size is from about 10 microns to about 7000 microns.

19. The method of claim 11 wherein the particle size is from about 10 microns to about 150 microns.

20. The method of claim 11 wherein the particle size is from about 200 microns to about 1000 microns.

21. The method of claim 1 further comprising administering a platelet-binding modulator.

22. The method of claim 14 wherein the targeting moiety is a targeting moiety selected from the group consisting of an antibody or fragment thereof, a ligand, a receptor, a hormone, a lectin, a cadherin, and binding fragments thereof.

23. The method of claim 1 wherein administering comprises administering using a catheter, microcatheter, needle, syringe, by a surgical procedure, or by manual placement.

24. The method of claim 11 wherein administering comprises administering using a catheter, microcatheter, needle, syringe, or by a surgical procedure.

25. The method of claim 12 wherein administering comprises administering using a catheter, microcatheter, syringe, by a surgical procedure, or by manual placement.

26. The method of claim 13 wherein administering comprises administering using a catheter, microcatheter, syringe, by a surgical procedure, or by manual placement.

27. The method of claim 11 wherein the particle is formed of a material capable of retaining collagen.

28. The method of claim 27 wherein the material is selected from the group consisting of polyvinyl alcohol (PVA); polystyrene; polycarbonate; polylactide; polyglycolide; lactide-glycolide copolymers; polycaprolactone; lactide-caprolactone copolymers; polyhydroxybutyrate; polyalkylcyanoacrylates; polyanhydrides; polyorthoesters; albumin; collagen; gelatin, polysaccharides; dextrans; starches; methyl methacrylate; methacrylic acid; hydroxylalkyl acrylates; hydroxylalkyl methacrylates; methylene glycol dimethacrylate; acrylamide, bisacrylamide; cellulose-based polymers; ethylene glycol polymers and copolymers; oxyethylene and oxypropylene polymers; polyvinyl acetate; polyvinylpyrrolidone and polyvinylpyridine; magnetic particles; fluorescent particles; animal cells; plant cells; macro-aggregated and micro-aggregated albumin; denatured protein aggregates; and liposomes; any of the above used singly or in combination.

29. The method of claim 27 wherein the material is selected from the group consisting of polylactide; polyglycolide; and lactide-glycolide copolymers.

30. The method of claim 27 wherein the material is selected from the group consisting of polyvinyl alcohol (PVA); polystyrene; polycarbonate; polycaprolactone; lactide-caprolactone copolymers; polyhydroxybutyrate; polyalkylcyanoacrylates; polyanhydrides; and polyorthoesters.

31. The method of claim 27 wherein the material is selected from the group consisting of methyl methacrylate; methacrylic acid; hydroxylalkyl acrylates; hydroxylalkyl methacrylates; and methylene glycol dimethacrylate.

32. The method of claim 27 wherein the material is selected from the group consisting of acrylamide, bisacrylamide; cellulose-based polymers; ethylene glycol polymers and copolymers, oxyethylene and oxypropylene polymers; polyvinyl acetate; polyvinylpyrrolidone and polyvinylpyridine.

33. The method of claim 27 wherein the material is selected from the group consisting of magnetic particles and fluorescent particles.

34. The method of claim 27 wherein the material is selected from the group consisting of animal cells and plant cells.

35. The method of claim 27 wherein the material is selected from the group consisting of macro-aggregated and micro-aggregated albumin; and denatured protein aggregates.

36. The method of claim 27 wherein the material is liposomes.

37. The method of claim 28 wherein the material is selected from the group consisting of polylactide; polyglycolide; lactide-glycolide copolymers; macro-aggregated and micro-aggregated albumin.

38. The method of claim 1 wherein the binding agent is bound on or in the solid phase agent.

39. The method of claim 38 wherein the binding agent is bound directly to the solid phase agent.

40. The method of claim 38 wherein the binding agent is bound directly to the solid phase agent using covalent or non-covalent binding.

41. The method of claim 38 wherein the binding agent is bound indirectly to the solid phase agent.

42. The method of claim 38 wherein the binding agent is bound indirectly to the solid phase agent using one or more spacers.

43. The method of claim 42 wherein the spacers are selected from one or more of the group consisting of peptide spacer arms, antibody spacers, antibody fragment spacers, fusion protein spacers and carbohydrate spacers.

44. The method of claim 43 wherein the antibody fragment spacer is an Fc portion of an antibody.

45. The method of claim 1 wherein the binding agent is immobilized on or within the solid phase agent using an antibody or antibody fragment.

46. The method of claim 1 wherein at the site of a vascularized tumor or hyperplastic tissue comprises an organ or associated vasculature.

47. A method of treating a vascularized tumor or hyperplastic tissue comprising administering to a pre-determined site at or near a vascularized tumor or hyperplastic tissue collagen bound to polylactide-co-glycolide, allowing the collagen to capture and activate platelets, and allowing the activated platelets to form a thrombus.

48. The method of claim 11 wherein the particle size is from about 150 microns to about 300 microns.

49. The method of claim 11 wherein the particle size is from about 300 microns to about 500 microns.

50. The method of claim 11 wherein the particle size is from about 500 microns to about 800 microns.

51. The method of claim 11 wherein the particle size is from about 800 microns to about 1000 microns.

* * * * *